(12) United States Patent
Lee et al.

(10) Patent No.: US 7,611,715 B2
(45) Date of Patent: Nov. 3, 2009

(54) AGARICUS EXTRACT FOR PREVENTING THE INDUCTION OR METASTASIS OF CANCER

(75) Inventors: Insu Peter Lee, Bethesda, MD (US); Tomihisa Ota, Ishikawa (JP)

(73) Assignee: SSI Co., Ltd., Tokyo (JP)

( * ) Notice: Subject to any disclaimer, the term of this patent is extended or adjusted under 35 U.S.C. 154(b) by 0 days.

(21) Appl. No.: 11/737,709

(22) Filed: Apr. 19, 2007

(65) Prior Publication Data

US 2007/0184066 A1 Aug. 9, 2007

Related U.S. Application Data

(63) Continuation of application No. 10/519,971, filed as application No. PCT/JP03/08157 on Jun. 26, 2003, now abandoned.

(30) Foreign Application Priority Data

| Jul. 2, 2002 | (JP) | ............................. | 2002-193943 |
| Nov. 5, 2002 | (JP) | ............................. | 2002-321864 |

(51) Int. Cl.
*A61K 36/00* (2006.01)
(52) U.S. Cl. ................................. 424/195.15
(58) Field of Classification Search ........................ None
See application file for complete search history.

(56) References Cited

U.S. PATENT DOCUMENTS

2002/0110564 A1 * 8/2002 Itokawa .................. 424/195.15
2004/0029955 A1 * 2/2004 Kouge et al. .................. 514/459

FOREIGN PATENT DOCUMENTS

| JP | 07-258107 | 10/1995 |
| JP | 11 113531 | 4/1999 |
| JP | 2000-038347 | 2/2000 |
| JP | 2001-010970 | 1/2001 |
| JP | 2002-145796 | 5/2002 |
| JP | 2002-308777 | 10/2002 |
| JP | 2003-128561 | 5/2003 |
| JP | 2003128561 | * 5/2003 |

OTHER PUBLICATIONS

See et al. (Immunology Investigations (May 2002), vol. 31, No. 2, pp. 137-153).*
Yu et al. (Eur. J. Biochem. (2000), vol. 267, pp. 2122-2126).*
Ito (Biotherapy (2000), vol. 14, No. 10, pp. 1009-1015—abstract).*
International Search Report (ISR) dated Aug. 19, 2003 from PCT/JP03/008157.
Kadosawa, et al., "Clinical Efficacy of *Agaricus blazei* Murill and/or Shark Cartilage in Dogs and Cats with Tumors", *Jpn. J. Small Anim. Pract.*, 20(2):101-109, 2001.

* cited by examiner

*Primary Examiner*—Susan C Hoffman
(74) *Attorney, Agent, or Firm*—Susan J. Myers Fitch; Peter J. Dehlinger; King & Spalding

(57) ABSTRACT

A foodstuff capable of preventing the induction or metastasis of cancer is provided. In particular, an *Agaricus blazei* Murill extract comprising an ingredient capable of preventing the induction or metastasis of cancer is provided. The ingredient can be a chromatographic main elute fraction of 100 to 2000 molecular weight, obtained by the steps of extracting the fruit body of *Agaricus blazei* Murill with hot water, dialyzing the resultant extract, and subjecting the thus obtained dialysis external fluid to chromatography. Alternatively, the ingredient can be a dialysis external fluid obtained by the steps of extracting the fruit body of *Agaricus blazei*Murill with hot water, adding ethanol to the resultant extract to thereby obtain precipitates, dissolving the precipitates in water, and dialyzing the solution.

5 Claims, 7 Drawing Sheets

AGARICUS EXTRACT FOR PREVENTING THE INDUCTION OR METASTASIS OF CANCER

This patent application is a continuation of U.S. patent application Ser. No. 10/519,971 filed Sep. 21, 2005 now abandoned, which is a national stage application under 35 U.S.C. § 371 of PCT/JP03/08157 filed Jun. 26, 2003, both of which are incorporated herein in their entirety by reference.

TECHNICAL FIELD

The present invention is directed to an *Agaricus blazei* Murill extract comprising an ingredient being capable of preventing the induction or metastasis of cancer. More specifically, the present invention is directed to an *Agaricus blazei* Murill extract for preventing the induction of cancer by urethane (ethyl carbamate, EC) existing in fermented foods and alcoholic beverages, carcinogen (4-N-methyl-N-nitroamino)-1-(3-pyridyl)-1-buthanone (NNK) existing in tobacco smoke or azoxymethane (AOM), or the metastasis of the cancer induced by urethane, NNK or AOM.

BACKGROUND ART

Urethane and NNK are known to induce a variety of cancers. Urethane has induced lung cancer and liver cancer in mouse in a dose dependent manner, and the safety dose (virtually safe dose, VSD) thereof in human have been calculated to be $1.8 \times 10^{-4}$ mg/kg bodyweight for lung cancer, and $7.2 \times 10^{5}$ mg/kg body weight for liver cancer, respectively (K. Inai et. al., Jpn. J. Cancer Res.,82, pp. 380-385, April, 1991).

Progeny of the mouse treated by urethane during pregnancy and lactation period have developed significantly increased embryotic cancer, lung cancer and ovarian cystadenoma through placenta, and parent pregnant mouse also have developed endometrial hyperplasia and uterus hemangioma (T. Nomura, Cancer Research, 33, 1677-1683, July, 1973).

Orally administered urethane has induced lung cancer, lymphoma, liver cancer, gastric papilloma, sebaceous gland tumor, breast cancer, lung ademoma, tumor of squamous epithelium cell, leukemia, mesenchymoma, and the like (IARC MONOGRAPHS ON THE EVALUATION OF THE CARCINOGENIC RISK OF CHEMICALS TO MAN, vol. 7, pp. 111-131, the views of two IARC Working Groups on the Evaluation of the Carcinogenic Risks of Chemicals to Man which met in Lyon, Feb. 4, to 11, 1974; and Jun. 18 to 24, 1974).

Further, urethane is an object of regulation in Canada, because it is produced in alcohol fermentation and contained at a predetermined level in a brewed beverage such as wine (Ethyl Carbamate in Alcoholic Beverages and Fermented Foods, ACS Symposium Series No. 484, Food Safety Assessment, edited by John W. Finley et al., pp. 419-428, American Chemical Society, 1992; Identification of Volatile Constituents from Grapes, J. Agric. Food Chem., vol. 24, no. 2, pp. 329-331, 1976; RATIONALE FOR THE ESTABLISHMENT OF GUIDELINES TO LIMIT ETHYL CARBAMATE LEVELS IN ALCOHOLIC BEVERAGES, BUREAU OF CHEMICAL SAFETY FOOD DIRECTORATE HEALTH PROTECTION BRANCH, HEALTH & WELFARE CANADA, pp. 1-8; Ethylcarbamate in Fermented Beverages and Foods, Cornelius S. Ough, J. Agric. Food Chem., vol. 24, No. 2, pp. 323-327.

NNK is one of the possible carcinogenic substances contained in a tobacco smoke (Djordijevic, M. V. et al., A Comparison of selected components in the mainstream smoke of the leading U.S. and Japanese cigarettes. In: Proceedings of the CORESTA smoke and Technology Meeting, pp. 200-217, Nov. 3 to 8, 1996). The morbidity of lung cancer is increasing significantly in both males and females.

The incidence of lung cancer is highly associated with smoking and alcohol ingestion. The International agency for Research on Cancer suggests that the amount of smoking and the amount of alcohol ingestion tend to increase synergistically in human, and that NNK and urethane ingested thereby are causes of lung cancer incidence.

Lung cancer accounts for 45% and 21.5% of cancer related deaths in males and females, respectively. Currently, lung cancer is becoming a leading cause of death in comparison to heart disease among those who smoke in America.

Accordingly, food ingredients, which prevent the induction of cancer caused by smoking and alcohol ingestion, have been sought.

The mushroom, which is generally called *agaricus*, belongs to the family *Agaricaceae* of the division *Basidiomycota*, and is referred to by the botanical name "*Agaricus blazei* Murill" and the Japanese name "kawariharatake". *Agaricus* (hereinafter, generally referred to as kawariharatake, ABM, or *agaricus*) has been traditionally used as a medicament in the Piedade region in Sao Paulo, Brazil. It is said that *agaricus* has a variety of immune activation activities, cancer prevention effects, tumor growth suppression effects, and the like. Currently, it is provided for internal use as health food.

Polysaccharides contained in *agaricus* include β-1, 6-glucopyranosyl residues and have antitumor activity against Sarcoma 180 (Ebina T et al. (1986), Jpn. J. Cancer Res 77:1034-1042). Extracts from *agaricus* include (1→4)-α-D-glucan having (1→6)-β branched chain, and have natural killer cell activation activity and selective antitumor activity mediated through apoptosis (Fujimiya Y et al. (1998), Cancer Immunol Immunother 46:147-159). Peptideglycans from *agaricus* have a direct cytotoxic activity against Meth A tumor cells in a double implanted tumor system and an indirect immune enhancement activity in tumor-bearing mice (Ebina T et al. (1998), Biotherapy 11:259-265). Polysaccharides contained in *agaricus* change the percentage of spleen Thy1,2-, L3T4 positive cells in a T cell subset of mice (Mizuno Metal. (1998), Biosci. Biotechnol. Biochem. 62:434-437).

These reports suggest that polysaccharides contained in *agaricus* have cytotoxic activity against tumor cells through an immunomodulation activity.

Thus, there have been many reports that say *agaricus* extracts have an immune enhancement activity and antitumor activity. However, in order to test the effects of *agaricus* extract, previous researchers have used in vitro tests or in vivo tests with animals which already have cancer. Accordingly, the effects of *agaricus* extracts on processes of induction and metastasis of cancer such as lung cancer, large intestine cancer, which are caused by a habit of living such as smoking or alcohol ingestion, have not been studied. It has not been reported that there is a food ingredient having effects on processes of inducing cancer and metastasizing cancer, to the best of inventor's knowledge. It is considered that this is because there is no reliable assay system for evaluating processes of inducing cancer and metastasis of cancer.

DISCLOSURE OF THE INVENTION

Materials for drugs or foodstuffs capable of potentially preventing the induction or metastasis of cancer are provided.

The present invention is directed to an *agaricus* extract or an ingredient contained therein which is capable of preventing the induction (incidence) or the metastasis thereafter of cancer. The inventor has completed the present invention by finding that an *agaricus* extract or an ingredient contained therein suppresses the genes or gene products which are overexpressed in A/J mouse being in the course of lung cancer induction by administering a carcinogenic substance, urethane or NNK, and by finding that an *agaricus* extract or an ingredient contained therein suppresses the formation of aberrant crypt foci (ACF) in rat being in the course of large intestine cancer induction by administering a carcinogenic substance, AOM.

Although it is not desired to be constrained by a particular theory, it is considered that *agaricus* extract prevents the induction and the metastasis thereafter of cancer by containing an effective ingredient or ingredients which inhibit the activation of a carcinogenic substance, or remove the possible free radical produced by the metabolism of a carcinogenic substance, or remove the free radical producer in a carcinogenic substance, or suppress the expression of oncogenes, or synergistic effects therebetween.

The present invention provides *agaricus* extract comprising an ingredient which is capable of preventing the induction and metastasis of cancer. According to one aspect of the present invention, the extract is prepared by extracting *agaricus* with a solvent.

The term "*agaricus*" used herein generally refers to *agaricus* materials comprising a fruit body, a mycelium, a culture broth and the like of a mushroom belonging to the family Agaricaceae of the division Basidiomycota, referred to by the botanical name "*Agaricus blazei* Murill" and the Japanese name "kawariharatake". The term "*agaricus*" typically means a fruit body of *agaricus*. Hereinafter, "kawariharatake", "ABM", and "*agaricus*" are used interchangeably, and they are terms indicating an identical *agaricus* material.

Preferably, the extract is prepared by extracting *agaricus* with hot water.

Preferably, the ingredient is a chromatographic main elute fraction of 100 to 2000 molecular weight obtained by the steps of extracting the (fruit body of) *agaricus* with hot water, dialyzing the resultant extract, and subjecting the thus obtained dialysis external fluid to chromatography.

Preferably, the ingredient is a dialysis external fluid obtained by the steps of extracting the fruit body of *agaricus* with hot water, adding ethanol to the resultant extract to thereby obtain precipitates, dissolving the precipitates in water, and dialyzing the solution.

The cancer can be those induced by urethane, (4-N-methyl-N-nitroamino)-1-(3-pyridyl)-1-buthanone or azoxymethane. Typically, the cancer is lung cancer or large intestine cancer.

The present invention is also directed to a composition being capable of preventing the induction or metastasis, comprising an *agaricus* extract, and a pharmaceutically acceptable carrier.

The composition can be in a form selected from the group consisting of powder, liquid, tablet, capsule and pellet.

BEST MODE FOR CARRYING OUT THE INVENTION

Figure 1:
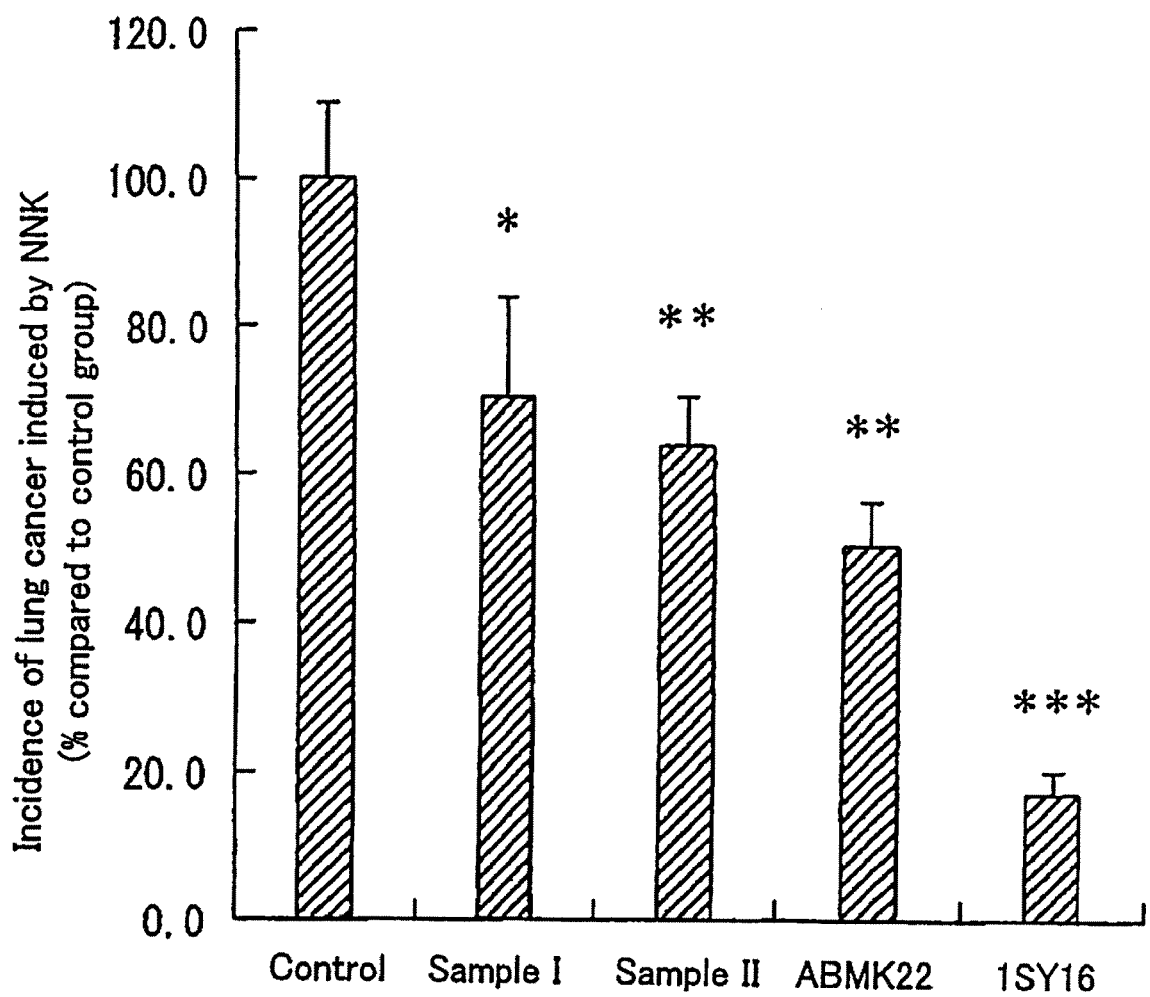
FIG. 1 shows that an *agaricus* extract of the present invention prevents the induction of lung cancer caused by NNK.

*Agaricus* extract of the present invention is prepared by extracting *agaricus* material with a solvent. The *agaricus* material is typically a naturally occurring or cultured fruit body of *agaricus*. Cultured mycelium of *agaricus* in a culture tank or the like may also be used. Normally, *agaricus* is used after washing followed by drying. Commercially available dried fruit body is also used conveniently. Normally, dried *agaricus* is pulverized according to a standard method, and used as a starting material for extraction.

The *agaricus* extract of the present invention can be obtained by conducting an extraction procedure after adding a solvent to the dried fruit body or a powder thereof. In general, the dried fruit body, or the powder thereof, is mixed with a solvent of 2 to 10 times the weight thereof to conduct extraction. As the solvent, water, ethanol, propanol, butanol, acetone, 1,3-butylene glycol, ethyl acetate, hexane, methylene chloride, methanol, or a mixture thereof is used. Typically, water is used to prepare an *agaricus* extract.

Extraction procedure is conducted by mixing the *agaricus* powder with any of the above described solvents, and stirring or shaking with a magnetic stirrer (100 to 500 rpm) and the like, the thus obtained mixture, at a temperature between 0 to 100° C., preferably at a temperature between room temperature to 80° C., for a period of between 10 minutes to several days, preferably between 1 to 24 hours. Typically, the *agaricus* extract can be obtained by adding deionized water to the *agaricus* powder, and continuously stirring for 24 hours at 70° C. The thus obtained solution is lyophilized after removing the residue by a standard method such as centrifugation, filtration, and the like. The thus obtained powder is an *agaricus* extract.

The ingredient or ingredients capable of preventing the induction or metastasis being contained in the thus prepared *agaricus* extract can be obtained by utilizing a method known to those skilled in the art such as HPLC (high performance liquid chromatography), and the like. The structure of the obtained ingredient can be identified using a technique such as NMR (nuclear magnetic resonance), and the like.

The following is an example of a preparation method for an *agaricus* extract of the present invention.

Water with 5 to 10 times the weight of dried fruit body is added, and followed by heat-extracting or heat-refluxing the mixture for 1 to 3 hours. This hot water extraction from *agaricus* may be performed using a residue previously extracted with hot water. The solution extracted with hot water thus obtained is dried by a method known to those skilled in the art such as lyophilization, spray-drying, or the like to obtain a dried product (hereinafter, referred to as dried product A). Dried product A is mixed with 5 to 20 times the weight thereof of water. Then, the solution is put into a dialysis tube and dialyzed for 10 to 15 hours with several times the amount thereof of distilled water. The obtained dialyzate (external fluid) is lyophilized to obtain a dried product (hereinafter, referred to as dried product C) containing an ingredient or ingredients which are capable of preventing the induction or metastasis of cancer.

Then, the solution remaining in the dialysis tube is further dialyzed against running water for 20 to 40 hours and dialyzed twice against a distilled water for a few hours each time and a dried product of the solution remaining in the dialysis tube is obtained as described above. Thus, the dried product (hereinafter, referred to as dried product B) containing any ingredient or ingredients which are capable of preventing the induction or metastasis of cancer can be obtained.

Next, the obtained dried product C is dissolved in about ten times the weight thereof of distilled water. Gel chromatography is performed with distilled water as an eluent to obtain 20 mL of fractions. From the obtained fractions, a fraction or fractions in the middle of the elution peak, which has a molecular weight of about 100-2000 Da by gel filtration, is an ingredient or ingredients which are capable of preventing the induction or metastasis of cancer of the present invention.

These fractions were analyzed further using reverse-phase chromatography, which uses ODS (octadecyl silanated silica gel), ion-exchange chromatography using DEAE-TOYOPEARL 650, or the like, and confirmed to include a plurality of ingredients such as arginine, lysine, mannitol, and the like.

The solution extracted with hot water, obtained by the above-described method, is mixed with an equal amount of ethanol. The mixture is centrifuged to separate a precipitate form a supernatant. The obtained supernatant is further mixed with ethanol of 1 to 3 volumes thereof. The mixture is further centrifuged to obtain a precipitate. The precipitate obtained is dissolved in distilled water and the solution obtained, is dialyzed. The dialyzate obtained is also an ingredient or ingredients which are capable of preventing the induction or metastasis of cancer of the present invention.

The *agaricus* extract or the ingredient or ingredients contained therein, which are capable of preventing the induction or metastasis of cancer, prepared as described above can be used for production of medicines by themselves or in combination with various carriers.

Typically, the *agaricus* extract or the ingredient or ingredients contained therein, which are capable of preventing the induction or metastasis of cancer, prepared as described above, can be formulated as a composition capable of being taken orally with a biocompatible pharmaceutical carrier (for example, physiological saline, buffered physiological saline, dextrose, water, and the like).

The above described pharmaceutically acceptable carriers are known to those skilled in the art and include, for example, the following carriers but not limited to these: buffers such as Ringer's solution, Hank's balanced salt solution, or buffered physiological saline; fatty acids such as sesame oil; synthetic fatty acid esters such as ethyl oleate or triglycerides; saccharides such as lactose, sucrose, mannitol, sorbitol; starches derived from vegetables such as corn, wheat, rice, or potato; cellulose such as methylcellulose, hydroxypropylmethylcellulose, or sodium carboxymethylcellulose; rubber such as gum arabic or tragacanth; proteins such as gelatin or collagen; cross-linked polyvinyl pyrrolidone, agar, alginic acid or salts thereof, or the like.

The *agaricus* extract or the ingredient or ingredients contained therein, which are capable of preventing the induction or metastasis of cancer, prepared as described above can be ingested alone or in combination with other drugs or foodstuffs.

The *agaricus* extract, or the ingredient or ingredients contained therein contained therein, which are capable of preventing the induction or metastasis of cancer, and the composition comprising them, prepared as described above, can be administered orally or parenterally. Parenteral administration is accomplished via intravenous, intramuscular, intraabdominal or intranasal administration. The details of formulation and administration of the pharmaceutical composition according to the present invention can be performed in accordance with descriptions in a textbook in the field of art, for example, "REMINGTON'S PHARMACEUTICAL SCIENCES" (Maack Publishing Co., Easton, Pa.).

The *agaricus* extract, or ingredient or ingredients contained therein which are capable of preventing the induction or metastasis of cancer for oral administration can be formulated as a composition including a pharmaceutically acceptable carrier well known in the art, in a prescription form suitable for ingestion. Such a carrier allows the composition obtained to be formulated as a tablet, pill, sugar-coated pill, capsule, liquid, gel, syrup, slurry, suspension, or the like, suitable for ingestion by patients.

The composition of the present invention includes the *agaricus* extract or ingredient or ingredients contained therein in an amount effective for preventing the induction or metastasis of cancer. Those skilled in the art will thoroughly understand and recognize the "pharmacologically effective amount for preventing the induction or metastasis of cancer". Initially, the "pharmacologically effective amount for preventing the induction or metastasis of cancer" can be evaluated by in vitro assay via cell culturing or an appropriate animal model. Then, using such information (obtained in the initial in vitro assay or animal model), the effective amount for ingestion inhuman can be determined. The "pharmacologically effective amount for preventing the metastasis of cancer" can be determined, for example, in the assay using A/J mouse in which lung cancer is induced by administering NNK, as described herein.

The amount of the *agaricus* extract which is actually ingested depends on the health conditions, or the like of the individual to which the extract is applied and may be optimized so that a desirable effect can be achieved. It is a routine process for those skilled in the art to determine a pharmaceutically or nutritionally effective amount.

The *agaricus* extract, or an ingredient or ingredients contained therein, capable of preventing the induction or metastasis can be mixed with one or more selected foodstuffs in an amount sufficient for exerting its function. The one or more selected foodstuffs are mixed with the fraction having immune activation activity in a form known to those skilled in the art, usually, powder form. The mixture can be served as a liquid food product depending on its utility or on preference. Alternatively, the mixture may be formed as capsules such as hard capsules or soft capsules, tablets, or pills, or may be formed into a powdery, granular, tea-leaf, tea-bag, or candy form.

The *agaricus* extract, or an ingredient or ingredients contained therein, contained therein, which are capable of preventing the induction or metastasis of cancer prepared as described above, inhibits lung cancer induced by NNK or urethane, and the metastasis thereof. The present invention is based on studies regarding therapies by *agaricus* extract in various administration forms against carcinogenic substances existing in fermented food, and those in tobacco smoke. In reference to procedures, protocols or guidance disclosed herein, the effectiveness of the above described *agaricus* extract, or an ingredient or ingredients contained therein contained therein, which are capable of preventing the induction or metastasis of cancer, against cancer induced by other carcinogenic substances, can be easily confirmed.

That is, the effectiveness of the above described *agaricus* extract, or an ingredient or ingredients contained therein, capable of preventing the induction or metastasis of cancer can be easily confirmed by examining the effects on expression level of the cyclin D1 gene and expression level of PCNA (an antigen of growing cell) in lung tissue of mouse to which a carcinogenic substance has been administered, caused by foods which contain varying concentrations of *agaricus* extract, or an ingredient or ingredients capable of preventing the induction or metastasis of cancer.

Similarly, the effectiveness of the above described *agaricus* extract, or an ingredient or ingredients contained therein, capable of preventing the induction or metastasis of cancer can be easily confirmed by examining whether or not the incidence of lung cancer in mouse, to which a carcinogenic substance has been administered, is inhibited; by examining whether or not the expression level of the cyclin D1 gene in lung tissue of mouse, to which a carcinogenic substance has been administered, is suppressed; and by examining whether or not the expression level of PCNA (an antigen of growing cells) in mouse lung tissue is suppressed, caused by foods which contain varying concentrations of *agaricus* extract, or an ingredient or ingredients being capable of preventing the induction or metastasis of cancer.

Hereinafter, the present invention will be further described by way of examples using urethane and NNK as carcinogens. The following examples are merely illustrative and do not limit the present invention.

EXAMPLES

Hereinafter, the present invention is illustrated by the following examples.

Example 1

Preparation of *agaricus* Extract (1) The above described dried product A was used as a *agaricus* hot water extract. This product A was obtained by extracting a dried fruit body of *agaricus* (Kyowa's *agaricus* mushroom (available from Kyowa Engineering Co., Ltd.)) with boiling water, removing residue by centrifugation, at 1800×g, for 10 minutes followed by lyophilization. The product A is dissolved in purified water at a concentration of 3.7 mg/ml to form Sample I, and at a concentration of 8 mg/ml to form Sample II.

(2) Distilled water (2 L) was added to 300 g of Kyowa's *agaricus* mushroom, and the mixture was heated to reflux for two hours. The solution obtained was filtered to separate a filtrate (a solution extracted with hot water) and a residue. Again, 2 L of distilled water was added to the residue and the mixture was heated to reflux for another two hours to perform hot water extraction and a filtrate was obtained. Further, the same procedure was repeated one more time. The filtrates obtained were lyophilized together to obtain dried product A (153 g: extraction rate of 51%).

Distilled water (500 mL) was added to 50 g of dried product A and the mixture was put into a dialysis tube (Spectra/Por Membrane 50×31, inner diameter of 8 mm and length of 30 cm, FE-0526-65). The mixture was dialyzed against 3 L of distilled water for 12 hours. The dialyzate obtained was lyophilized to obtain dried product C (27 g: extraction rate of 53%). The solution remaining in the dialysis tube was further dialyzed against running water for 30 hours, and then dialyzed twice against distilled water (four hours each time, total 8 hours). Thereafter, the solution remaining in the dialysis tube was lyophilized to obtain dried product B (11 g: extraction rate of 22%). Subsequently, 3 g of dried product C was dissolved in 30 mL of distilled water and chromatography using TOYOPEARL HW40C (inner diameter of 40 mm and length of 420 mm) was performed. The eluent was entirely distilled water. For each fraction, 20 ml of the aliquots were taken to obtain fractions 1 to 30. These fractions were divided into the following five groups with reference to results of thin-layer chromatography analysis. The dried weights were as follows: fractions 1 to 11 (75 mg, 2.5%); fractions 12 to 15 (920 mg, 30.7%); fractions 16 to 17 (1570 mg, 52.3%); fractions 18 to 19 (270 mg, 9%); and fractions 20 to 28 (97 mg, 3.2%).

Infrared radiation (IR) absorption spectrum data of fraction 16 (hereinafter, referred to as 1SY-16) was as follows.

Fraction 16: IR (KBr) 3390, 3325, 3285, 2940, 2920, 1641, 1634, 1622, 1615, 1600, 1595, 1405, 1394, 1084, 1020: molecular weight (estimated by gel filtration) 100-2000 Da (3) Hot water extraction similar to that described above was performed to obtain 6 L of a combined filtrate (a solution extracted with hot water). The filtrate was concentrated under reduced pressure to 1 L, and 1 L of ethanol was added thereto and mixed followed by centrifugation to obtain precipitate and supernatant. Ethanol (3 L) was further added to the supernatant and mixed, and the mixture was centrifuged to obtain a precipitate, and the precipitate was dissolved in distilled water and dialyzed. The external dialyzate obtained was lyophilized to obtain a powder (hereinafter referred to as ABMK-22).

Example 2

Prevention of Lung Cancer Induced by NNK, by Means of *Agaricus* Extract

Fifty A/J mice (male, 7 weeks age) were divided into 5 groups, which were administered with Sample I, Sample II, ABMK22, and 1SY16 described in Example 1, as well as a control group, respectively. NNK (4 mg per kg body weight) was administered via a single gavage to each mouse in each group. This amount of NNK administered to each mouse corresponds to the amount of NNK which would have been ingested during one hundred years, if a person were to smoke a box of tobacco per day (Djordijevic, M. V. et al., Comparison of selected components in the mainstream smoke of the leading U.S. and Japanese cigarettes. In: Proceedings of the CORESTA smoke and Technology Meeting, pp. 200-217, Nov. 3 to 8, 1996). Subsequently, the *agaricus* extract was administered to each mouse of each group as described below.

Control Group: Mice Allowed to Freely Ingest Normal Drinking Water

Sample I group: mice allowed to freely ingest drinking water containing 30% (v/v) of Sample I for 16 weeks.

Sample II group: mice allowed to freely ingest drinking water containing 60% (v/v) of Sample II for 16 weeks.

The amount of water ingested by each mouse in the above described groups, was about 5 ml/mouse/day, respectively.

ABMK22 group: ABMK22 was administered via a gavage at a dose of 100 mg/kg body weight for 7 days.

1SY16 group: 1SY16 was administered via a gavage at a dose of 100 mg/kg body weight for 7 days.

Mice in each group were sacrificed 16 weeks after administering NNK and dissected, and the incidence of lung cancer was examined using a dissection observation microscope. The results are shown in FIG. 1. The horizontal axis in FIG. 1 indicates each test group, and the vertical axis indicates the incidence of lung cancer (the morbidity of lung cancer in each group provided that the morbidity of the control group is made to be 100%).

As indicated in FIG. 1, *agaricus* extract reduced significantly the incidence of lung cancer as compared with the control group (the results in Sample I group and Sample II group, showed significant difference at $P<0.05$ and $P<0.01$, respectively, as compared with the control group. Significance for Sample I group and Sample II group is represented by * and **, respectively in FIG. 1), and ingredients ABMK22 and 1SY16 containing in *agaricus* extract further reduced the incidence of lung cancer as compared with the *agaricus* extract (the results for ABMK22 group and 1SY16 group, are statistically significant at $P<0.01$ and $P<0.001$, respectively as compared with the control group. Significance for ABMK22 group and 1SY16 group is represented by as  and *, respectively in FIG. 1). In the event that the results are represented as the ratio of suppression (100 minus the ratio of incidence), as seen in FIG. 1, the ratio of suppression for Sample I, Sample II, ABMK22 and 1SY16 were about 30%, about 35%, about 50% and about 82%, respectively.

In this way, it was shown that the ingestion or administration of *agaricus* extract and ingredients contained therein suppressed the generation of cancer induced by NNK.

Example 3

Prevention of Lung Cancer Induced by NNK, by Means of *Agaricus* Extract

Figure 2:
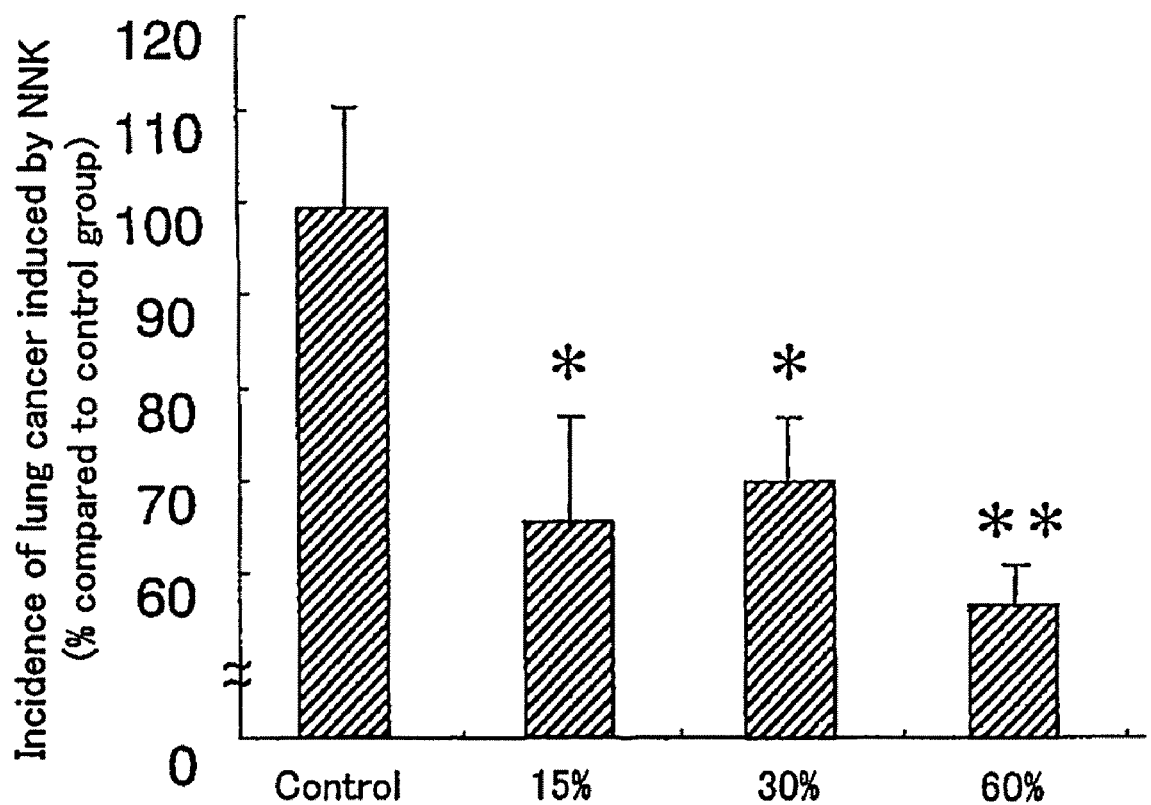
FIG. 2 shows that an *agaricus* extract of the present invention prevents the induction of lung cancer caused by NNK in a dose dependent manner.

Control group, and three test groups, each of which was allowed to freely ingest drinking water containing 15% (v/v), 30% (v/v) or 60% (v/v) of the above described Sample II were provided, and lung cancer was induced by NNK similarly as described in Example 2. Subsequently, similar to Example 2, mice in each group were sacrificed 16 weeks after administering NNK and dissected, and the incidence of lung cancer was examined using a dissection observation microscope. The results are shown in FIG. 2. The horizontal axis in FIG. 2 indicates each test group, and the vertical axis indicates the incidence of lung cancer (the morbidity of lung cancer in each group provided that the morbidity of the control group is made to be 100%).

As indicated in FIG. 2, *agaricus* extract reduced significantly the incidence of lung cancer as compared with the control group (the results in test groups, each of which was allowed to freely ingest drinking water containing 15% (v/v), 30% (v/v) or 60% (v/v) of Sample II, showed significant difference at $P<0.05$, $P<0.05$ and $P<0.01$, respectively as compared with the control group. They are represented by * and **, respectively in FIG. 2).

In this way, it was shown that the ingestion or administration of *agaricus* extract and ingredients contained therein suppressed the generation of cancer induced by NNK in a dose dependent manner.

Example 4

Suppression of Gene or Gene Product Induced by Administering NNK, by Means of *Agaricus* Extract The above described Sample I, ABMK22, and 1SY16 were administered to each group of A/J mice, which were grouped similarly as in Example 2 except for not providing a group receiving Sample II. Similar to Example 2, mice in each group were sacrificed 16 weeks after administering NNK and dissected, and the expression of cyclin D1, proliferating cell nuclear antigen (PCNA), and the expression of cyclin-dependent kinase 4 (CDK4) in lung tissue was examined. Cyclin D1, PCNA, and CDK4 were measured according to the method described in I. P. Lee, Pulmonary cyclin D1-induction by Fumonisin B1 in Female A/J mice, The 91th Cancer Society: Paper No. 5313, Apr. 15, 2000.

Generally speaking, cells during growth have a cell cycle comprised of division phase (M phase) and inter phase (G1 phase, S phase and G2 phase). DNA synthesis occurs in a part of inter phase (S phase). The genetic information is replicated in S phase and is equally divided in M phase into two daughter cells.

CDK4 is a member of the protein phosphorylating enzyme family, and controls advancement through the cell cycle. Therefore, CDK 4 is so to speak, an engine of cell cycle advancement. Cyclin D1 has a role to advance cells in G1 phase to S phase by combining with CDK4. Cyclin D1 plays a role, so to speak, as an accelerator, and as a regulating factor for CDK4. PCNA is a subunit of DNA polymerase which advances cells into S phase, and thus also corresponds to an engine for advancing the cell cycle. The aberrant overexpression of these proteins leads to the induction of cancer, and thus, genes encoding these proteins are oncogenes. It is possible to evaluate whether or not cells are in the process leading to the incidence of cancer by analyzing these gene products.

Figure 3:
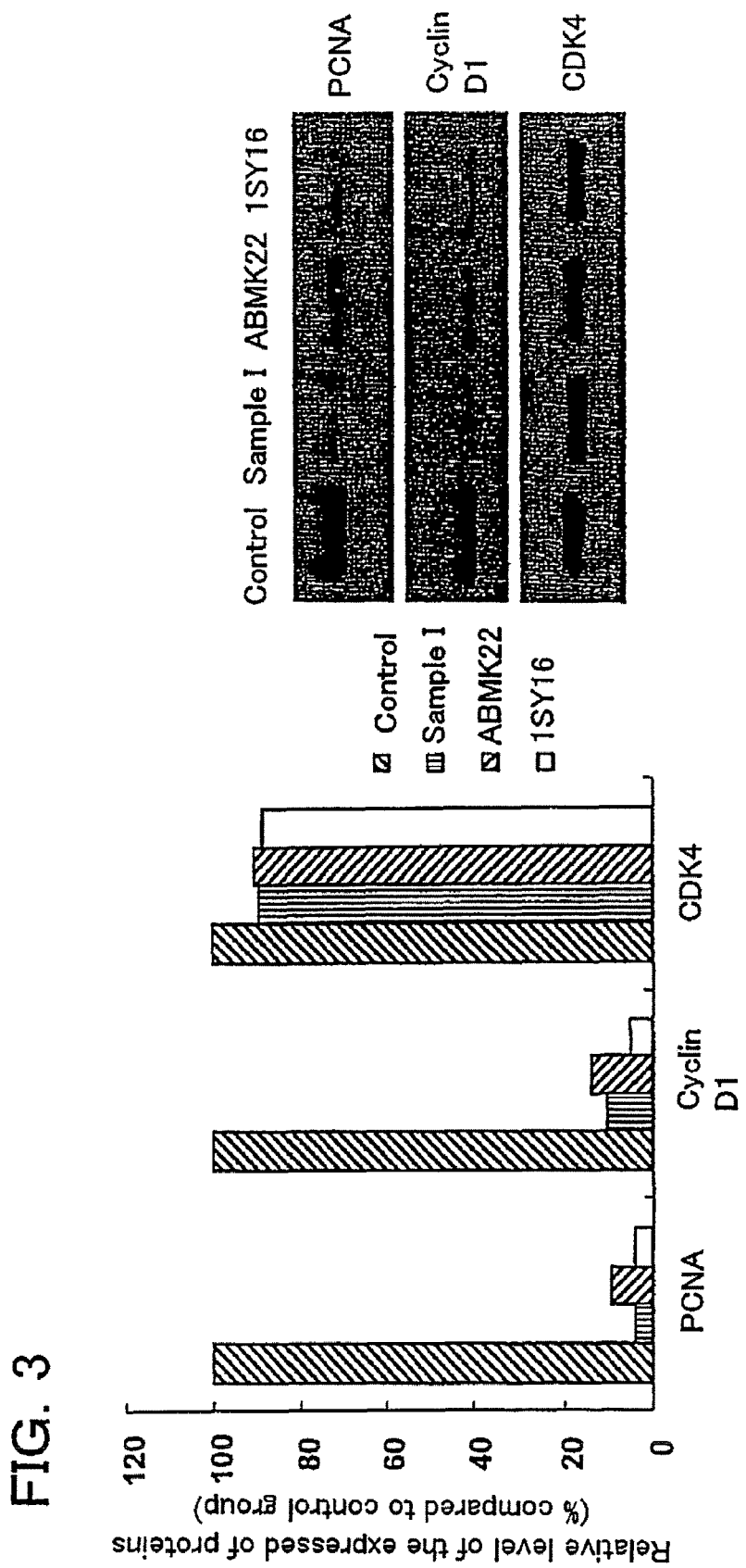
FIG. 3 shows that an *agaricus* extract of the present invention suppresses a gene or a gene product induced by administering NNK.

FIG. 3 shows the results of measuring expression of PNCA, cyclin D1 and CDK4 in lung tissue of A/J mice in each group. Right-hand portion of FIG. 3 indicates bands of PCNA, cyclin D1 and CDK4 when lung samples in each group were subject to electrophoresis. Light and shade represent strength of the expression level. As indicated in the right-hand portion of FIG. 3, PNCA, cyclin D1 and CDK4 in the control group are expressed abnormally as dense bands were detected, as such cancer has been induced. However, in groups being administered with Sample I, ABMK22, and 1SY16, less dense bands of PCNA and cycline D1 are detected indicating that these proteins have not expressed abnormally. The left-hand portion of FIG. 3 represents the quantified results in each group as a bar graph. The vertical axis represents the amount of expression provided that the amount of expression in the control group was made to be 100%, and the horizontal axis represents PCNA, cyclin D1, and CDK4 expression in each group. Four bars in each measured item represent, left to right, control group, Sample I group, ABMK22 group, and 1SY16 group. As indicated in the left-hand portion of the figure, the expression levels of PCNA and cyclin D1 in Sample I group, ABMK22 group, and 1SY16 group were less than 10% compared with the expression level in control group (statistically significant differences at $P<0.01$).

In this way, it was shown that the ingestion or administration of *agaricus* extract and ingredients contained therein suppressed the expression of the oncogenes induced by NNK.

Example 5

Suppression of Gene or Gene Product Induced by Administering NNK, by Means of *agaricus* Extract Similar to Example 4, the expression of cyclin D1, proliferating cell nuclear antigen (PCNA), and cyclin-dependent kinase 4 (CDK4) in lung tissues was examined from mice allowed to freely ingest drinking water containing 15, 30 or 60% of Sample II.

Figure 4:
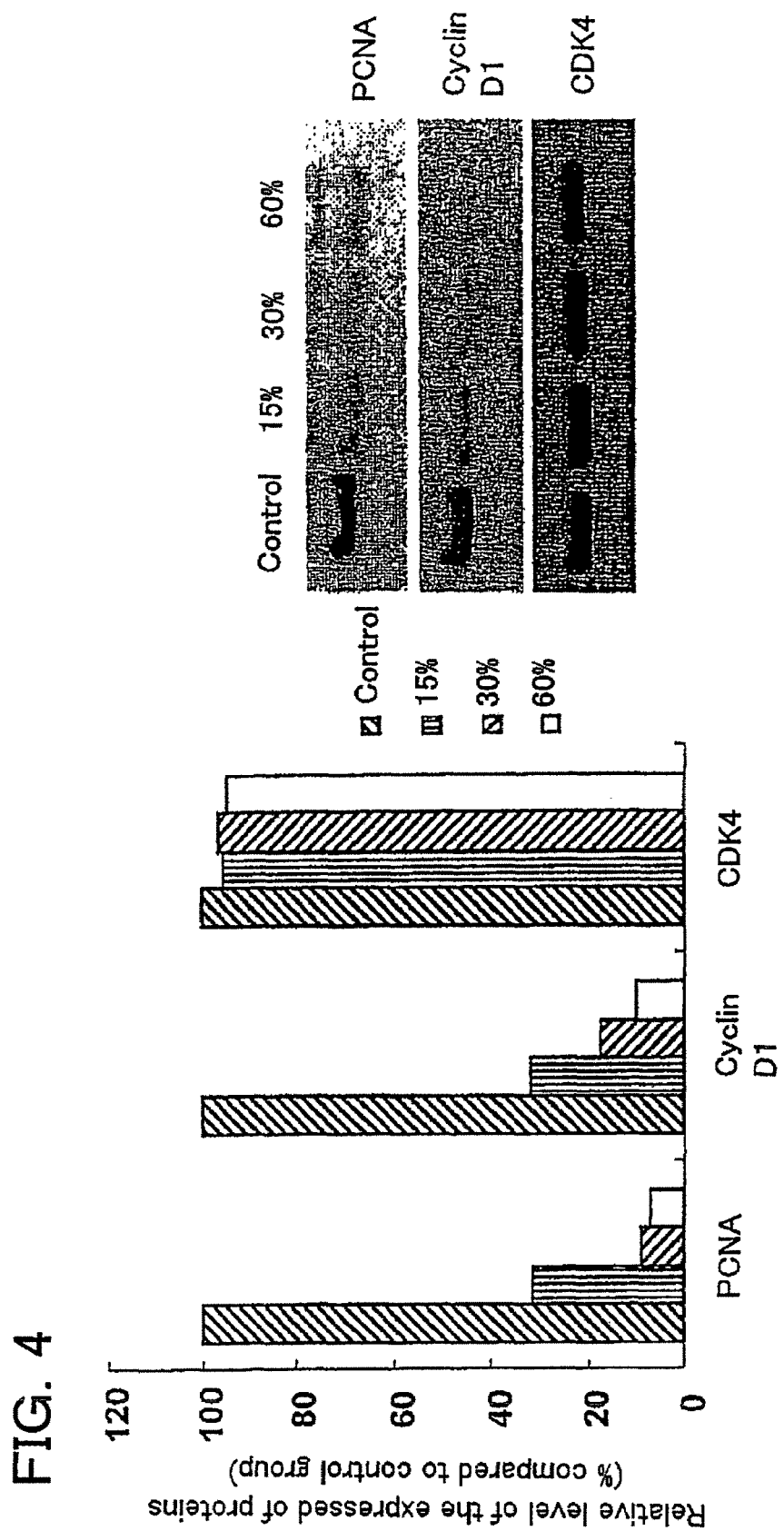
FIG. 4 shows that an *agaricus* extract of the present invention suppresses a gene or a gene product induced by administering NNK in a dose dependent manner.

FIG. 4 shows the results of measuring expression of PNCA, cyclin D1 and CDK4 in A/J mice of each group. The right-hand portion of figure in FIG. 4 indicates bands of PCNA, cyclin D1 and CDK4 when lung samples in each group were subject to electrophoresis. Light and shade represent strength of the expression level. As indicated in the right-hand portion of FIG. 4, PNCA, cyclin D1 and CDK4 in the control group are expressed abnormally, as dense band were detected, as such cancer has been induced. However, in groups being administered with drinking water containing 15, 30 or 60% of Sample II, less dense bands of PCNA and cycline D1 are detected, the higher the concentration of Sample II became, which indicated that Sample II suppressed the abnormal expression of these proteins in a dose dependent manner. The left-hand portion of FIG. 4 represents the quantified results in each group as a bar graph. The vertical axis represents the amount of expression provided that the amount of expression in the control group was made to be 100%, and the horizontal axis represents measured PCNA, cyclin D1, and CDK4 expression in each group. Four bars in each measured item represent, left to right, control group, groups ingesting drinking water containing 15, 30% or 60% of Sample II, respectively. As indicated, Sample II was indicated to suppress the abnormal expression of these proteins in a dose dependent manner (in groups ingesting drinking water containing 15, 30% or 60% of Sample II, the expression of cylcin D1and PCNA showed statistically significant differences at P<0.01, compared with the expression of cylcin D1 or PCNA in control group).

In this way, it was shown that the ingestion or administration of *agaricus*extract and ingredients contained therein suppressed the expression of the oncogenes induced by NNK in a dose dependent manner.

Example 6

Prevention of Lung Cancer Induced by Urethane, by Means of *Agaricus* Extract

Tests were conducted similar to Example 2, except for providing groups allowed to freely ingest drinking water containing 30% (v/v) Sample I, and 30% Sample II, respectively, and a group administered with ABMK22 as described in Example 2. In addition, instead of NNK, urethane was administered by a gavage in an amount about 20,000 times the exposure level in human (250 mg/kg mouse body weight).

Figure 5:
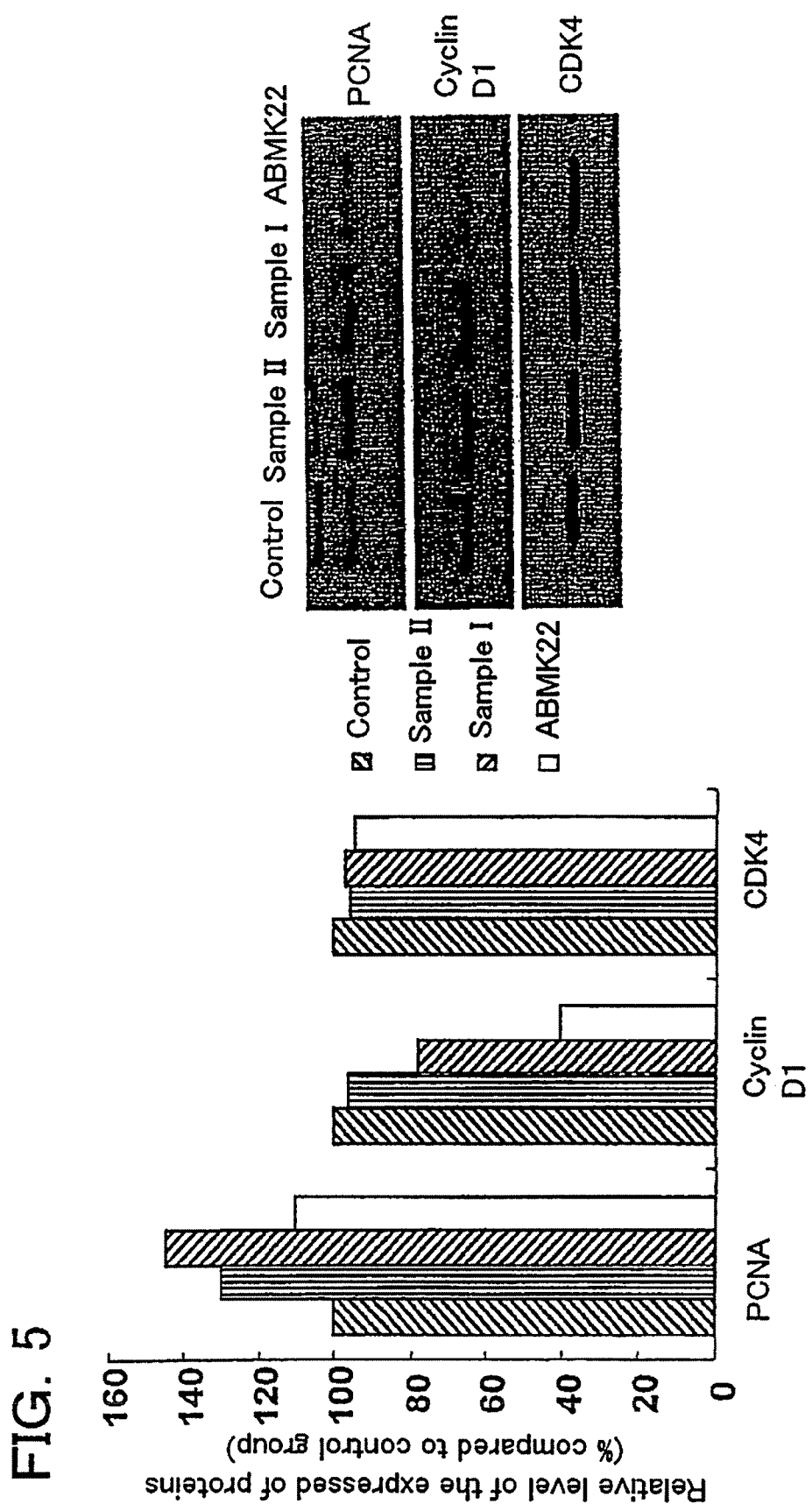
FIG. 5 shows that an *agaricus* extract of the present invention prevents the induction of lung cancer caused by urethane.

Similar to Example 2, mice in each group were sacrificed 16 weeks after administering urethane and dissected, and the incidence of lung cancer was examined using a dissection observation microscope. The results are shown in FIG. 5. The horizontal axis in FIG. 5 indicates each group tested, and the vertical axis indicates the incidence of lung cancer (the morbidity of lung cancer in each group provided that the morbidity of the control group is made to be 100%).

As indicated in FIG. 5, *agaricus* extract reduced significantly the incidence of lung cancer as compared with the control group (the results in test groups, showed statistically significant differences in Sample I group at P<0.05, and in Sample II group at P<0.01, as compared with the control group. They are represented by * and , respectively in FIG. 5**). ABMK22 contained in *agaricus* extract further reduced the incidence of lung cancer, compared with *agaricus* extract (the result showed statistically significant differences at P<0.001, as compared with the control group. Significance is represented by * in FIG. 5). In the event that the results are represented as the ratio of suppression (100 minus the ratio of incidence), as seen in FIG. 5**, the ratio of suppression for Sample I, Sample II, and ABMK22 was about 30%, about 60%, and about 82%, respectively.

In this way, it was shown that the ingestion or administration of *agaricus* extract and ingredients contained therein suppressed the generation of cancer induced by urethane.

Example 7

Prevention of Genes or Gene Products Induced by Urethane, by Means of *agaricus* Extract Tests were conducted similar to Example 2, except for providing groups allowed to freely ingest drinking waters containing 30% (v/v) Sample I, and 30% Sample II, respectively, and a group administered with ABMK22 as described in Example 2. In addition, as well as instead of NNK, urethane was administered by a gavage in an amount about 20,000 times the exposure level in human (250 mg/kg mouse body weight).

Similar to Example 4, the expression of cyclin. D1, proliferating cell nuclear antigen (PCNA), and cyclin-dependent kinase 4 (CDK4) in lung tissues of each group was examined.

Figure 6:
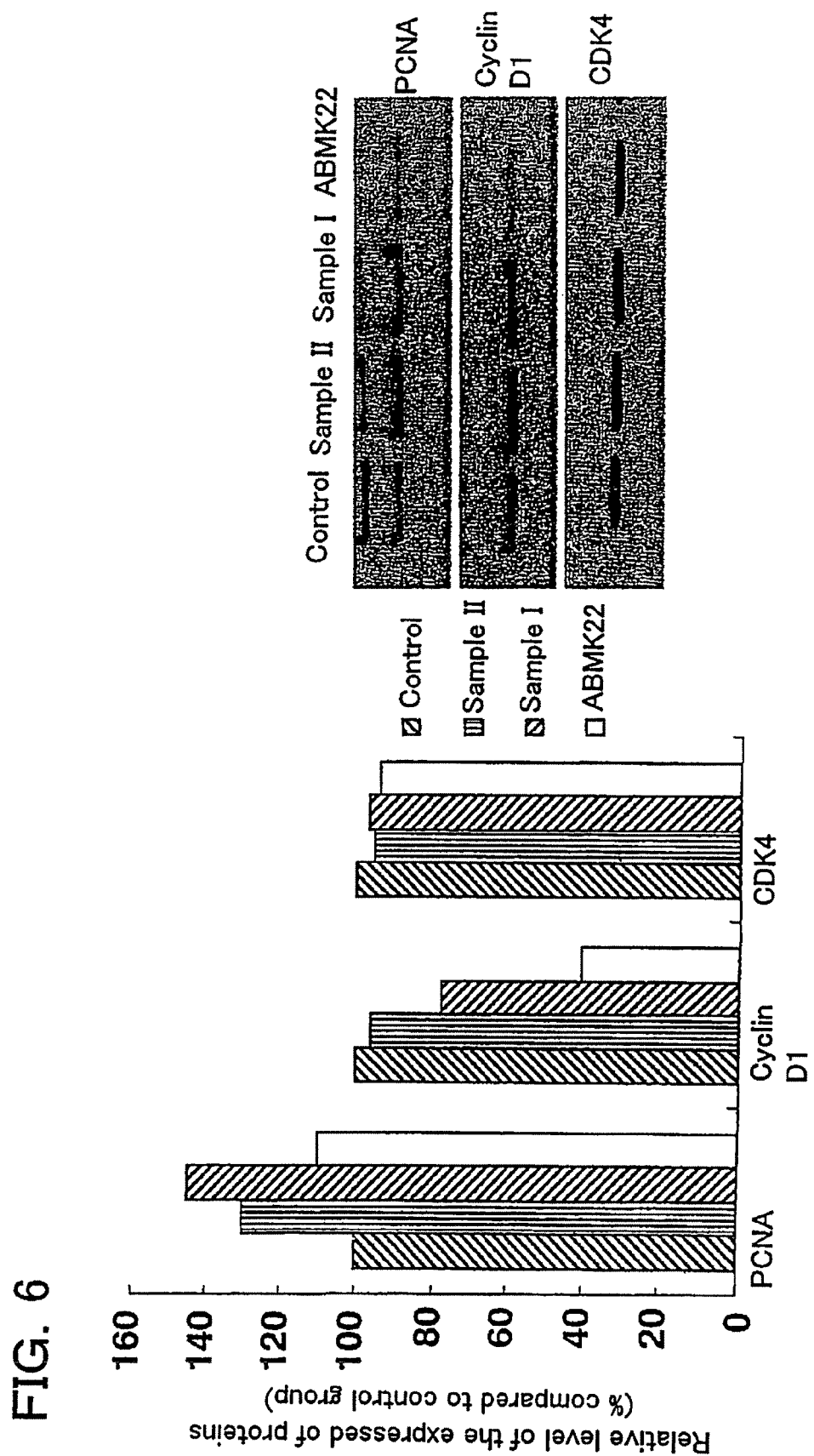
FIG. 6 shows that an *agaricus* extract of the present invention suppresses a gene or a gene product induced by administering urethane.

FIG. 6 shows the results of measuring expression of PNCA, cyclin D1 and CDK4 in A/J mice of each group. The right-hand portion of FIG. 6 indicates bands of PCNA, cyclin D1 and CDK4 when lung samples in each group were subject to electrophoresis. Light and shade represent strength of the expression level. As indicated in the right-hand portion of FIG. 6, PNCA, cyclin D1 and CDK4 in the control group are expressed abnormally, as dense bands were detected, as such these proteins were expressed abnormally at a high level, and the cancer has been induced. However, in groups allowed to ingest drinking water containing Sample I and Sample II, and the group administered with ABMK22, each band was less dense compared with the control group, indicating that abnormal expression of each gene has been suppressed. The left-hand portion of FIG. 6 represents the quantified results in each group as a bar graph. The vertical axis represents the amount of expression, provided that the amount expression in the control group was made to be 100%, and the horizontal axis represents measured PCNA, cyclin D1, and CDK4expression in each group. Four bars in each measured item represent, left to right, control group, groups ingesting drinking water containing Sample I, and Sample II, and a group administered with ABMK22. As indicated in the figure, especially ABMK22 was indicated to suppress the abnormal expressions of these genes (statistically significant differences at P<0.05).

In this way, it was shown that the ingestion or administration of *agaricus* extract suppressed the expression of the oncogenes induced by urethane.

Example 8

Prevention of Rat Colon Cancer Induced by AOM, by Means of *agaricus* Extract

It has been known that azoxymethane (AOM) is a carcinogenic substance which induces large intestine cancer and forms aberrant crypt foci (ACF) (Carcinogenesis 21(6):1149-1155, 2000). β-catenin gene often has been mutated in colon cancer in mouse and rat induced by AOM (Takahashi M. et. al., Carcinogenesis, 21:1117-1120.2000). In aberrant dysplasi ACF, both of modified intracellular localization of β-catenin and increased expression of inducible type nitrogen mono oxide synthetase (iNOS) were detected, but not detected in hyperplasia ACF (Takahashi M. et. al., Carcinogenesis, 21:1319-1327, 2000). Accordingly, ACF in mouse and rat induced by AOM can be used as an assay system for evaluating the process in which cancer is being induced, and the process in which cancer is metastasizing.

By using ACF induced by AOM as an assay system, it was evaluated whether or not an ingredient or ingredients contained in *agaricus* extract prevents the induction of cancer.

Thirty rats (female, 8 to 9 weeks age) were divided into 3 groups with each group consisting of 10 rats, which were the 1SY16 administered groups (120 mg/kg body weight group and 60 mg/kg body weight group), and the control group. To each rat of each group, 15 mg/kg body weight of AOM was injected twice a week subcutaneously.

Subsequently, rats of each group, were administered *agaricus* extracts as indicated below. 1SY16 was dissolved in a solution of 0.1% carboxymethylcellulose, and administered in a dose of 0.5% of body weight. Administration occurred twice a week, and continued for four weeks.

120 1SY16 group: 1SY16 was administered by a gavage in a dose of 120 mg/kg body weight.

60 1SY16 group: 1SY16 was administered by a gavage in a dose of 60 mg/kg body weight.

Control group: carboxymethylcellulose was administered by a gavage in a dose of 0.5% of body weight.

Figure 7:
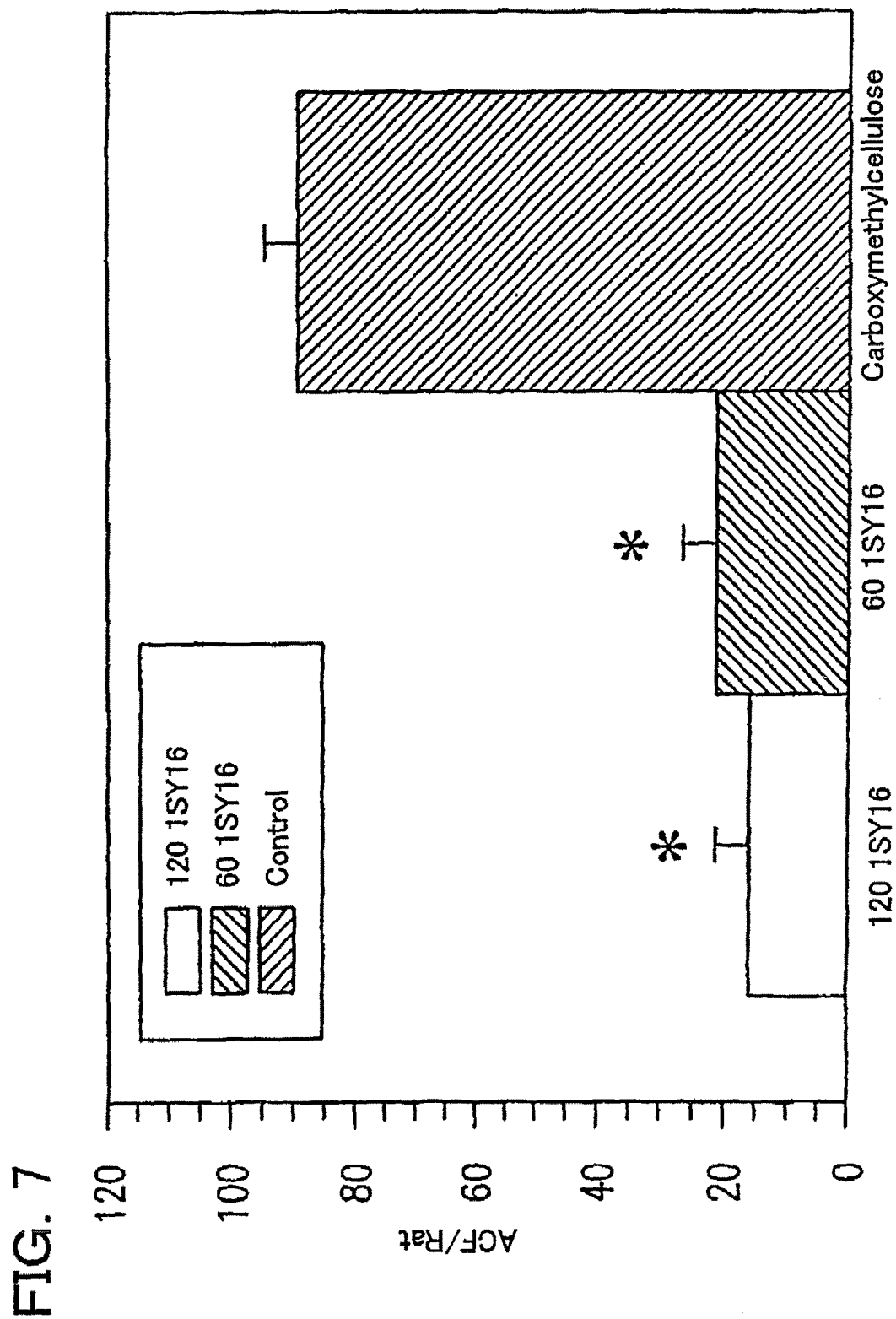
FIG. 7 shows that an *agaricus* extract of the present invention prevents the induction of large intestine cancer caused by AOM.

Mice in each group were sacrificed 13 weeks after administering AOM and dissected, and the numbers of ACF were counted using a dissection observation microscope. The results are shown in FIG. 7. The horizontal axis in FIG. 7 indicates each group tested, and the vertical axis indicates the average numbers of generated ACF per mouse.

As indicated in FIG. 7, 1SY16 reduced the numbers of generated ACF significantly compared with the control group (significant differences at $P<0.05$, indicated by * in FIG. 7). In the event that they are represented as the ratio of suppression, it is confirmed that the incidence of large intestine cancer in groups administered with 1SY16 of 60 mg/kg body weight and 120 mg/kg body weight were suppressed by about 72% and 82.5%, respectively, compared with the control group, indicating that the ingestion or administration of 1SY16 suppressed the generation of cancer induced by AOM.

As indicated above, since the ingestion or administration of *agaricus* extract or ingredients contained therein suppressed the expressions of a gene or gene product increased by the administrations of NNK and urethane in a dose dependent manner, it is considered that an ingredient or ingredients which suppress the carcinogenic conditions induced by the carcinogenic substance are contained in *agaricus* extract.

INDUSTRIAL APPLICABILITY

Material for drugs and foodstuffs which prevents the induction and metastasis of cancer potentially are provided. More specifically, material for drugs and foodstuffs which prevents the incidence of lung cancer by carcinogenic substances targeting lung, and the metastasis which occurs as a result thereof are provided.

The invention claimed is:

1. A method for inhibiting induction of a cancer, metastasis of a cancer, or both, wherein the cancer is selected from lung or large intestine cancer, and wherein said cancer is caused by a carcinogen, said method comprising
    administering a pharmacologically effective amount of extract from *agaricus*, wherein the extract is a chromatographic elute fraction of 100 to 2000 molecular weight obtained by the steps of extracting the fruit body of *agaricus* with water, dialyzing the resultant extract, and subjecting the thus obtained dialysis external fluid to chromatography.

2. A method for inhibiting induction of a cancer, metastasis of a cancer, or both, wherein the cancer is selected from lung or large intestine cancer, and wherein said cancer is caused by a carcinogen, said method comprising
    administering a pharmacologically effective amount of extract from *agaricus*, wherein the extract is a dialysis external fluid obtained by the steps of extracting the fruit body of *agaricus* with water, adding ethanol to the resultant extract to thereby obtain precipitates, dissolving the precipitates in water, and dialyzing the solution.

3. The method according to claim 1 or claim 2, wherein the cancer is induced by urethane (ethyl carbamate), NNK ((4-N-methyl-N-nitroamino)-1-(3-pyridyl)-1-buthanone) or azoxymethane.

4. A method for inhibiting metastasis of large intestine cancer wherein the cancer is caused by a carcinogen, said method comprising
    administering a pharmacologically effective amount of extract from *agaricus*.

5. The method according to claim 4, wherein the cancer is induced by urethane (ethyl carbamate), NNK ((4-N-methyl-N-nitroamino)-1-(3-pyridyl)-1-buthanone) or azoxymethane.

* * * * *

UNITED STATES PATENT AND TRADEMARK OFFICE
CERTIFICATE OF CORRECTION

PATENT NO. : 7,611,715 B2 Page 1 of 1
APPLICATION NO. : 11/737709
DATED : November 3, 2009
INVENTOR(S) : Insu Peter Lee and Tomihisa Ota It is certified that error appears in the above-identified patent and that said Letters Patent is hereby corrected as shown below:

On the title page, item (73), should read:
SSI Co., Ltd., Tokyo (JP)
Kyowa Hakko Kogyo, Co., Ltd. (JP)

Signed and Sealed this

Twentieth Day of April, 2010

David J. Kappos
*Director of the United States Patent and Trademark Office*